United States Patent
Dunn, Jr.

[11] Patent Number: 5,515,877
[45] Date of Patent: May 14, 1996

[54] DENTURE CLEANING DEVICE

[76] Inventor: Robert Dunn, Jr., 227 Red Hill Rd., Fremont, N.C. 27830

[21] Appl. No.: 225,571

[22] Filed: Apr. 11, 1994

[51] Int. Cl.⁶ ........................................ B08B 3/02
[52] U.S. Cl. ................ 134/111; 134/166 R; 134/169 R; 134/182; 134/201
[58] Field of Search ................... 134/103.1, 111, 134/184, 186, 191, 166 R, 169 R, 183, 182, 201; 366/166, 165

[56] References Cited

U.S. PATENT DOCUMENTS

| | | | |
|---|---|---|---|
| 158,684 | 1/1875 | Cosgrove | 134/111 |
| 392,517 | 11/1888 | King | 134/111 |
| 671,466 | 4/1901 | Brockett | 366/166 |
| 2,014,084 | 9/1935 | Kingsley et al. | 134/111 |
| 2,205,053 | 6/1940 | Thackeray | 366/166 |
| 2,609,828 | 9/1952 | Ward | 134/166 R |
| 2,669,243 | 2/1954 | Reynolds et al. | 134/200 X |
| 3,009,468 | 11/1961 | Eberle | 134/200 X |
| 3,098,496 | 7/1963 | Milbourne | 134/200 X |
| 3,207,481 | 9/1965 | Ranson | 134/166 R |
| 3,376,878 | 4/1968 | Shoemaker | 134/183 |
| 3,386,706 | 6/1968 | Leifman et al. | 134/184 |
| 3,606,274 | 9/1971 | Nelson | 134/184 |
| 4,005,854 | 2/1977 | Patton | 366/165 |

FOREIGN PATENT DOCUMENTS

| | | | |
|---|---|---|---|
| 1416979 | 10/1975 | United Kingdom | 134/184 |

*Primary Examiner*—Frankie L. Stinson
*Attorney, Agent, or Firm*—John G. Mills and Associates

[57] ABSTRACT

This invention is a dental cleaning device disposed within a visually attractive furniture grade cabinet. The cleaning tank within the device is kidney shaped with a pair of inlets that direct a circulating liquid upwardly and inwardly from an area adjacent the bottom of one end of said tank. At least one liquid outlet is provided at the opposite end of said tank and connected to a circulating means such as a circulating pump so that a continuous flow of liquid can be accomplished across dentures placed in the tank. The kidney shape of the tank causes eddy currents to flow off of the main swirling inlet to outlet liquid circulation to further clean the various areas of the dentures.

5 Claims, 4 Drawing Sheets

DENTURE CLEANING DEVICE

FIELD OF INVENTION

This invention relates to cleaning means and more particularly to denture cleaning devices.

BACKGROUND OF INVENTION

People who wear dentures have always had a problem cleaning the same. The accepted method of doing this is to place the dentures overnight in a container with a specially formulated cleansing solution which loosens plaque and food particles so that the same can be washed away when the dentures are removed from the container and rinsed prior to further use. After eating, when extended soaking is not possible, the artificial dentures can be removed, brushed and placed back in the mouth of the user but this a laborious job and one that most artificial denture users do not relish the thought of.

A variety of devices are available for mechanically cleaning artificial dentures from means for vibrating the soaking solution to propeller driven circulating means. All of these mechanical denture cleaners are primarily to help remove food and other matter from the dentures as a supplement to the overnight soaking.

All of the prior known mechanical denture cleaners and similar devices are either clinical in appearance or worse and are certainly not the type of devices that would be a pleasant addition to bathroom decor.

The following references represent the closest prior art of which the inventor is aware:

CONCISE EXPLANATION OF REFERENCES

U.S. Pat. No. 3,392,964 to Krolik et al discloses a vibratory device for cleaning dentures or the like and includes a magnetic coil that sets up ultrasonic vibration in the cleansing liquid 46 to loosen and remove foreign articles from the surfaces of the dentures or other articles contained therein.

U.S. Pat. No. 3,376,878 to Shoemaker discloses a cleaning bath with a multi-bladed agitator 18 to develop both sonic vibration and swirling of the liquid cleaning chemicals.

U.S. Pat. No. 3,132,657 to Ciccone, U.S. Pat. No. 3,265,369 to Harrison and U.S. Pat. No. 3,421,528 to Gomez et al all have mesh-like containers which hold artificial dentures that are immersed in a cleaning solution with rotating impellets below such containers for aiding in the cleansing of the dentures.

U.S. Pat. No. 2,746,467 to Dempsey et al is an apparatus adapted to clean foreign matter from objects such as machinery and parts thereof and is simply an elongated tube with an elbow at the end thereof and a motor and shaft that extends down into such tube. A propeller is on the end of the shaft to create circulation in the cleaning fluid. This arrangement requires a relatively large reservoir to establish the circulation described and would not be suitable for denture cleaning.

U.S. Pat. No. 2,469,825 to Hornstein and U.S. Pat. No. 3,378,019 to Riolo et al disclose, respectively, an automatic print washer and a parts washer. Both of these references show a horizontal swirling flow in the cleaning liquid but would not be suitable for denture cleaning since the center of the established vortex would have very little if any flow movement and certainly not strong enough to clean dentures.

U.S. Pat. No. 2,772,421 to Friend is an apparatus for hydrotherapeutic treatment which is basically a hot tub with a discharge elbow facing one way and an intake elbow facing the opposite way. A hose 7 with a nozzle 9 is also included so that therapeutic water flow can be directed to particular parts of the body. This apparatus obviously would not be suitable for denture cleaning.

U.S. Pat. No. 4,995,409 to Watts discloses an automobile parts washer utilizing a volatile cleaning solution while U.S. Pat. No. 3,500,840 to Maatz is a cleaning and sterilizing apparatus for barbering tools.

Finally, U.S. Pat. No. 2,679,253 to Carson is an apparatus for cleaning dishes prior to washing and having a means for separating tableware from garbage.

These last three mentioned references would not be suitable for denture cleaning and certainly do not anticipate the present invention as hereinafter set forth.

BRIEF DESCRIPTION OF INVENTION

After much research and study into the above-mentioned problems, the present invention has been developed to provide a relatively simple and yet highly-efficient means for cleaning artificial dentures. It is particularly adapted to remove food particles therefrom when the user does not have time to soak the dentures and does not want to take the time or make the mess that brushing causes.

The above is accomplished through the use of a small circulation pump that forces water or other cleaning fluids through two inlet ports in an upwardly and inwardly direction creating a swirling effect with secondary eddy currents in the liquid that washes against the surfaces of the artificial dentures. The single outlet port draws the fluid out of the cleaning tub to circulate it back through the inlet ports. This method of cycling the cleaning fluid at a gentle speed across the denture surfaces greatly reduces the time for cleaning the same and can be used by those on the go who need to freshen up but do not have time to brush the artificial dentures or allow the same to soak.

The exterior of the present invention is an attractive wooden cabinet that would be a pleasant addition to the decor of any bathroom. Once the artificial denture cleaning has been accomplished using the present invention, the cleaning solution is simply poured into the bathroom sink and the system flushed or rinsed with water which is then poured into the sink and the device is ready for its next use.

A filter is provided on the outlet of the tub and when the cleaning fluid is poured out, it can simply be back washed over the filter to remove food particles and other debris therefrom prior to filling the tub with rinse water.

OBJECTS OF THE INVENTION

In view of the above, it is an object of the present invention to provide a cleaning device for artificial dentures that creates a special swirling action with secondary eddy currents that removes food particles from the same when the user does not have time to brush or soak his or her dentures.

Another object of the present invention is to provide an improved artificial denture cleaning device that includes an impervious denture tub with a pair of upwardly and inwardly disposed inlets on one side and an outlet on the opposite side to create a cleansing swirling effect to remove food particles from said dentures.

Another object of the present invention is to provide, in a denture cleaning device, an attractive furniture grade cabinet that makes a pleasant addition to the bathroom decor.

Other objects and advantages of the present invention will become apparent and obvious from a study of the following description and the accompanying drawings which are merely illustrative of such invention.

DETAILED DESCRIPTION OF INVENTION

Figure 1:
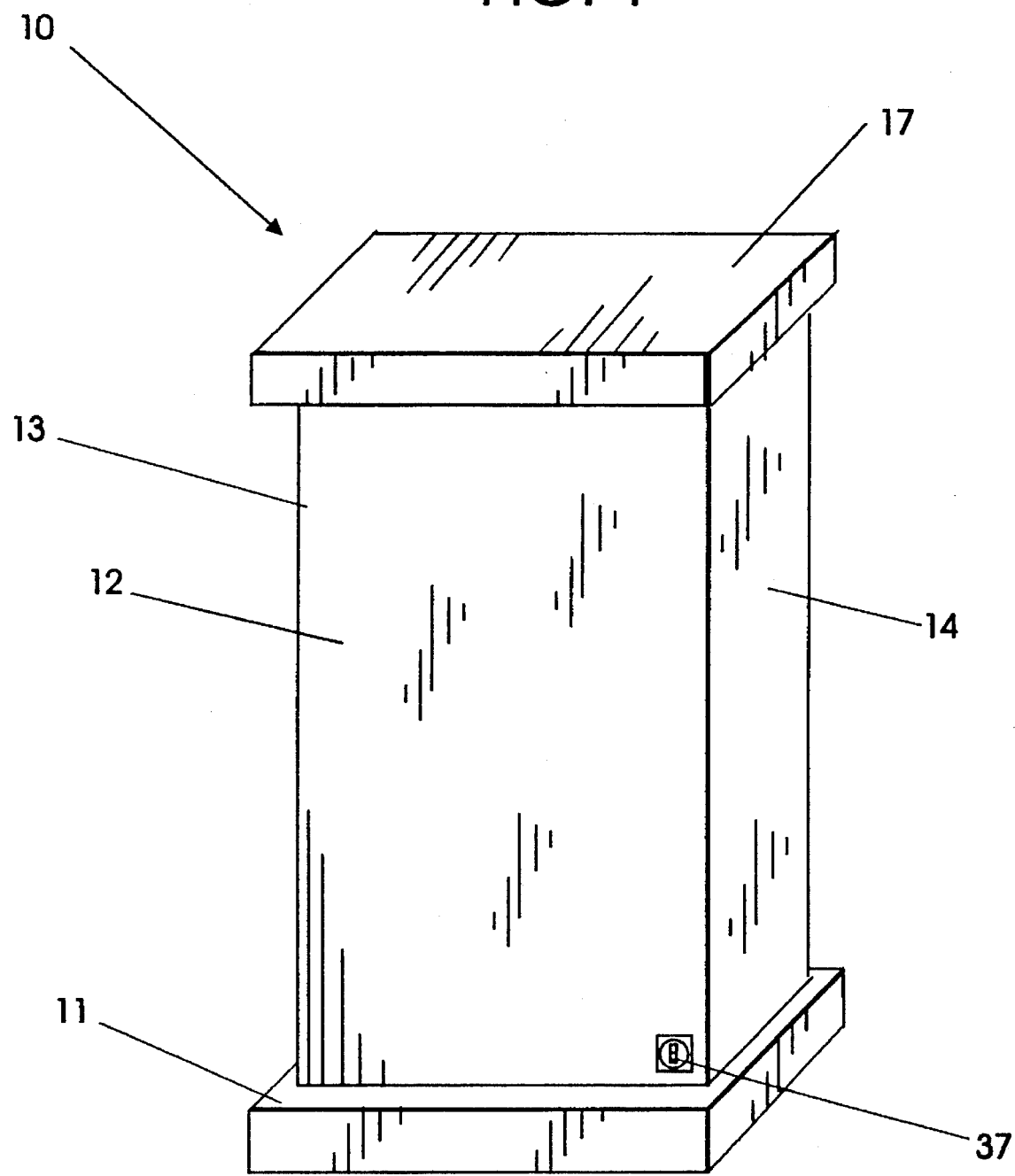
FIG. 1 is a front perspective view of the denture cleaning device of the present invention.
Figure 2:
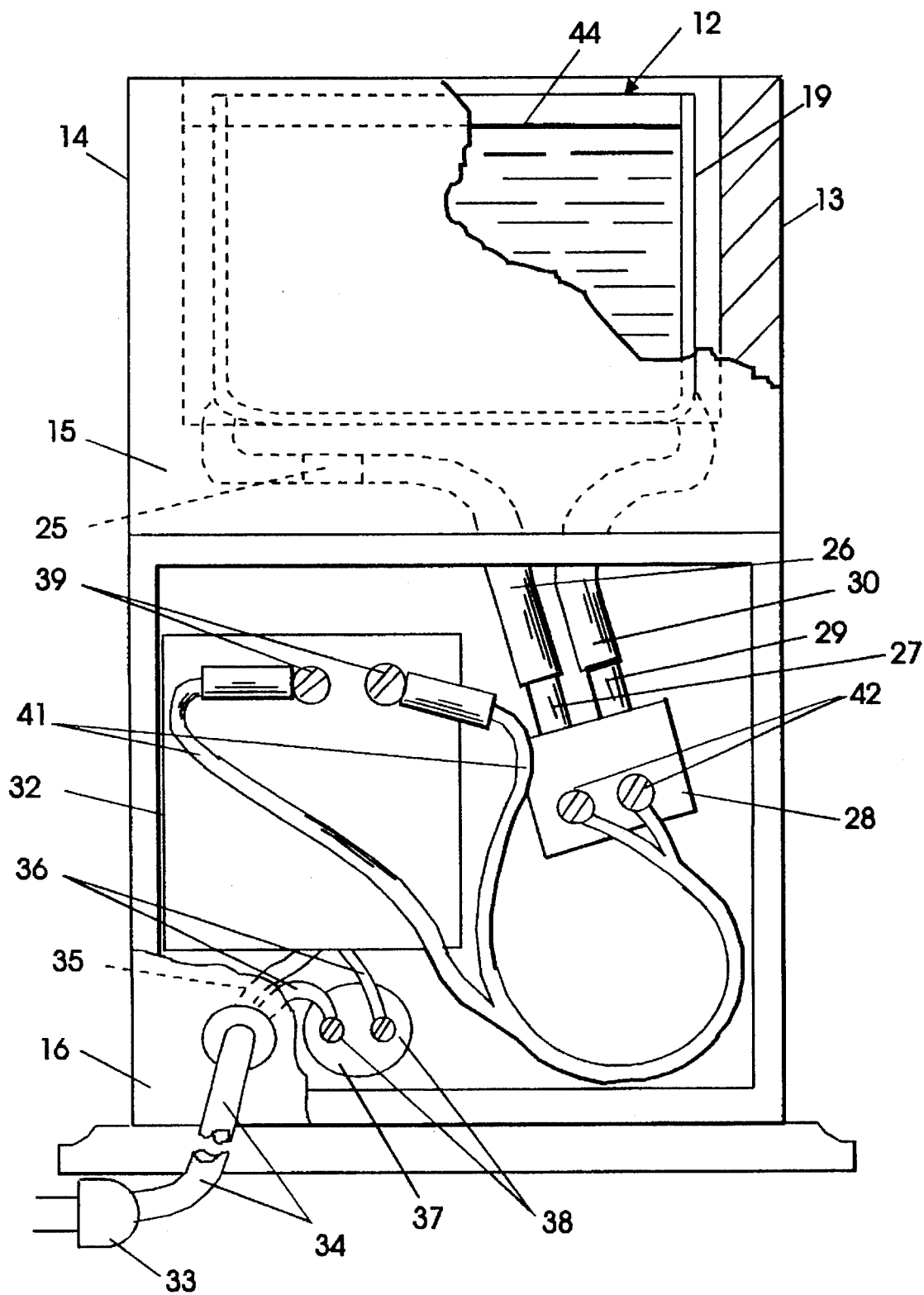
FIG. 2 is a partially cutaway, rear elevational view thereof.
Figure 3:
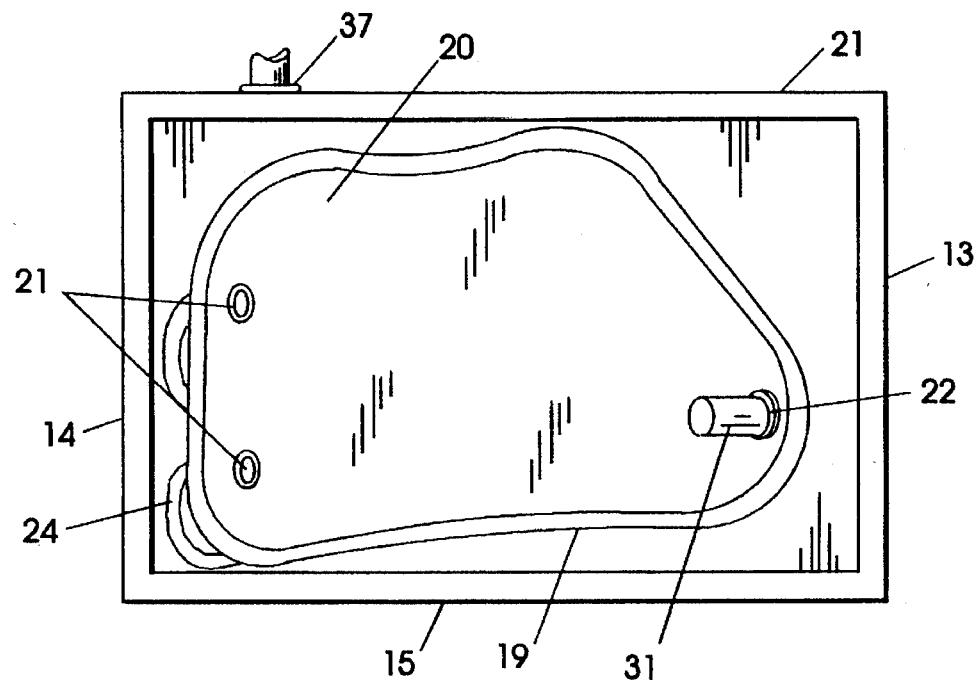
FIG. 3 is a top plan view of the cleaning device with the top removed.

With further reference to the drawings, the denture cleaning device of the present invention, indicated generally at 10, includes a base 11, an attractive front panel 12, sidewalls 13 and 14 and a rear wall 15 with a removable rear access panel 16. Finally, a top or lid 17 is provided which can be either hinged or of the lift-off type.

The entire exterior of the dental cleaning device 10 of the present invention is preferably produced from furniture grade wood or wood grain plastic to give a pleasing appearance and to enhance the decor of the bathroom or the location where the device is kept.

The denture cleaning tank, indicated generally at 18, includes side walls 19 and a bottom 20.

A pair of inlets 21 are provided in one end adjacent the bottom 20 and an outlet 22 is provided at the other end thereof. The inlets 21 are preferably at the curved transition between the bottom 20 and the side walls 19 and are aimed inwardly and upwardly while the outlet 22 is in a slight recess 23 in the bottom 20.

The inlets 21 are communicatively connected to a pair of inlet lines 24 at one end and to a Y-coupling at the other end. The third leg of the Y-coupling 25 is connected to inlet line 26 which is operatively connected to the outlet coupling 27 of circulating pump 28. The inlet coupling 29 of circulating pump 28 is operatively connected to one end of outlet line 30 with the other end connected to tank outlet 22. A tank outlet screen 31 is mounted on the end of the tank outlet to strain larger pieces of food and other waste which might damage the circulating pump 28 if allowed to flow therethrough.

The circulating pump 28 is preferably a direct current or DC type circulating pump. If standard 110 volts alternating current or AC is used as the primary source of power, then an inverter 32 is required to change the AC to DC. Since inverters of this type are well known to those skilled in the art, further detailed discussion of the same is not deemed necessary.

An AC line plug 33 can be plugged into any convenient AC source (not shown) which, through power cord 34, will deliver one side of the electrical current to the inverter 32 through wire 35. The other wire 36 of the power cord is operatively connected to the terminals 38 of off/on switch 37.

The DC terminals 39 of inverter 32 each have a wire 40 and 41 leading therefrom to the DC terminals 42 of the circulating pump 28.

Off/on switch 37 is preferably of the toggle-type and is operatively mounted through the front panel 12 of the denture cleaning device 10 of the present invention as can clearly be seen in FIG. 1. This switch can also be of the pre-set timer type or can include a variable timer feature. Since electrical wiring hookups and devices as described above are well known to those skilled in the art, further detailed discussion of the same is not deemed necessary.

The tank 18 of the present invention can either be kidney shaped as shown in the drawings or can be generally rectangular in shape. It has been found, however, that the kidney shaped tank that is wider at the inlet end than the outlet end with one side slightly concave before tapering to a rounded point gives considerably more swirling action with eddy currents than other shapes. This swirling action washes the dentures placed in the tank from different directions with the currents passing from outlet to inlet being caused to meander back and forth around the dentures due to the interaction of the dentures and the kidney shape tank sides.

To use the dental cleaning device of the present invention, the dentures 43 are placed in the tank 18 and the same is filled with a liquid 44 such as water and a dental cleanser. The switch 37 can then be turned on and the cycle timed or if the is a timer switch, it will automatically turn off when the predetermined time has expired.

Figure 4:
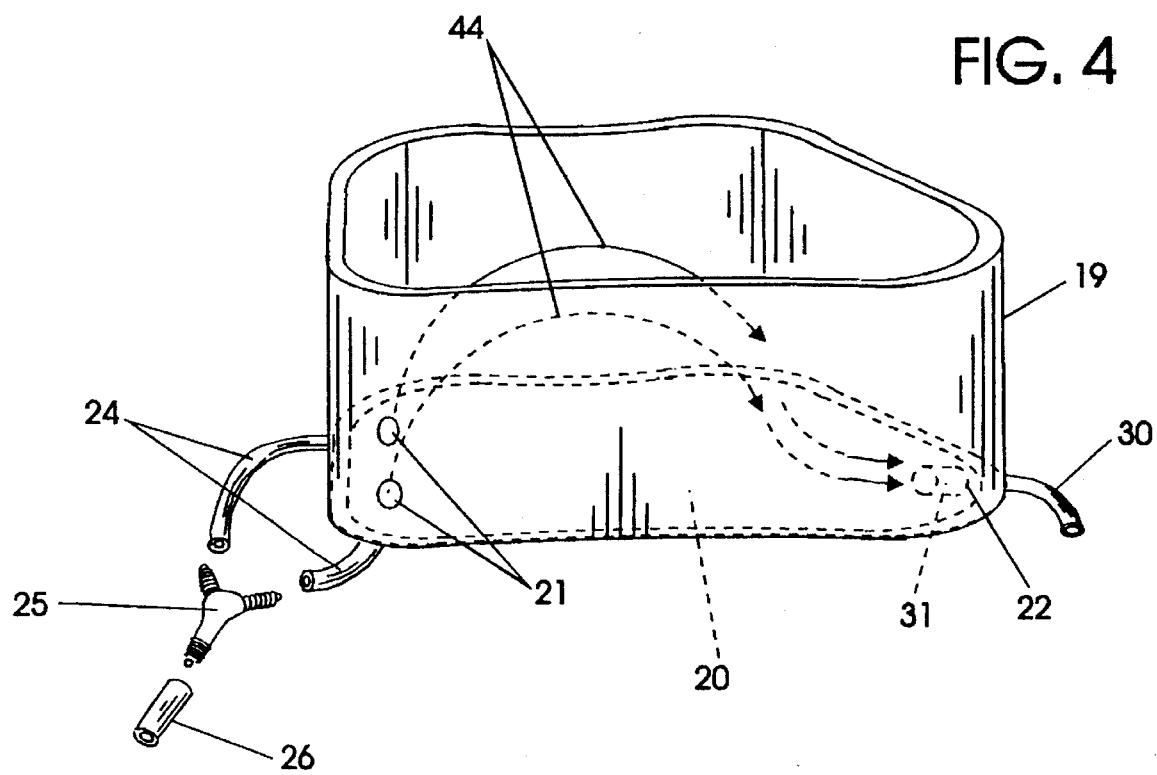
FIG. 4 is an exploded, somewhat schematic perspective view of the cleaning tank and its inlet and outlet lines.
Figure 5:
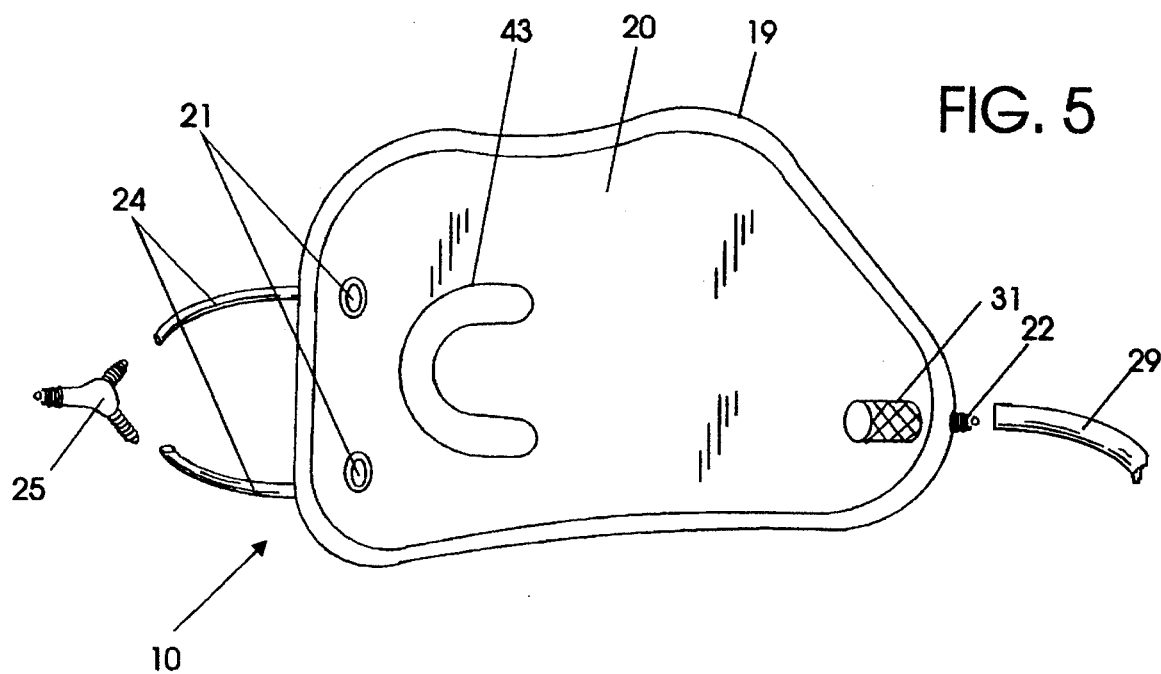
FIG. 5 is an exploded top plan view of said tank.
Figure 6:
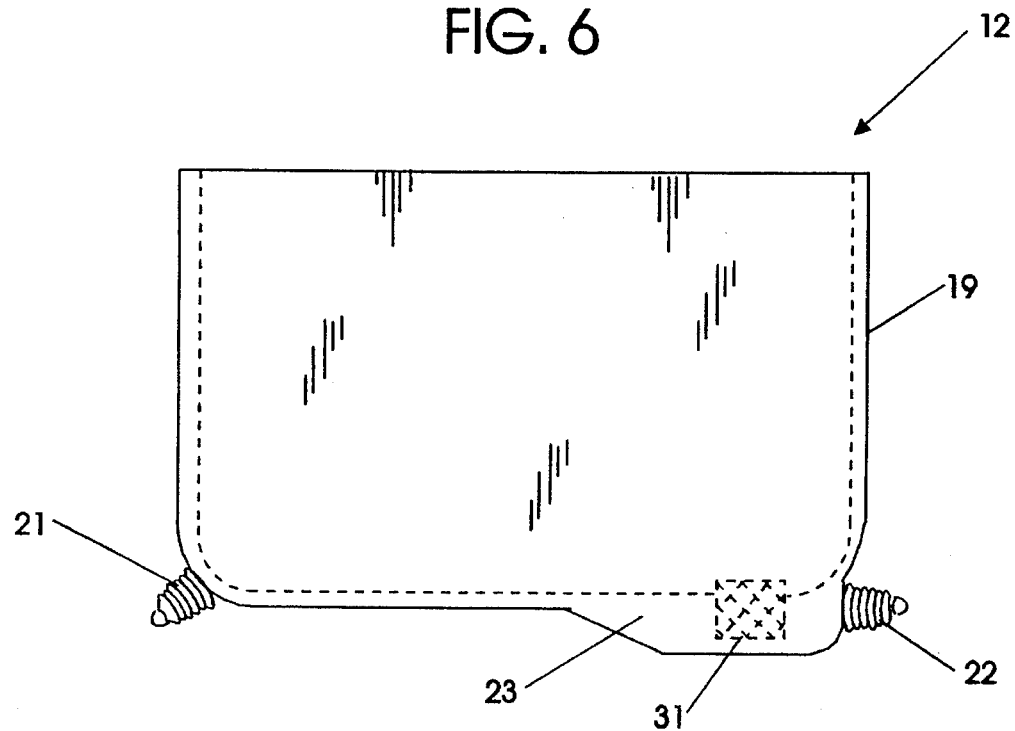
FIG. 6 is a side elevational view thereof.

In any case the inlets 21 which are disposed inwardly and upwardly cause a swirling action as indicated by the arrows 45 in FIG. 4. These swirling currents will meander back and forth creating subcurrents across the various surfaces of the dentures 43 prior to the liquid entering outlet 22 after passing through screen filter 31. Liquid passing out of the outlet goes through line 30 to the circulating pump 28 which then forces the liquid back through line 26 and into the tank 18 through inlet ports 21 for continuous swirling and cleansing of the dentures so long as the pump 28 is on.

The circulating of the liquid across the dentures greatly reduces the time required for cleaning over the soaking method.

Individuals who are unable to brush because of disability or those who need to freshen up their dentures without lengthy soaking can run the swirling circulation of the present invention for a short time to accomplish the same results.

The nonabrasive dental cleanser added to water during use of the present invention acts as a flushing agent and keeps the circulatory system clean and free of contaminants.

Once the system of the present invention has been used for cleansing the dentures, the user can simply pour the mixture of water and cleansing solution into the bathroom sink and refill the tank 18 with clean water to rinse the dentures and the denture cleaning system 10 of the present invention by again circulating water through such system.

The rinse water can then be poured into the sink and the denture cleaning device 10 of the present invention is ready for the next cleaning cycle when additional water and dental cleanser would be added.

From the above it can be seen that the present invention has the advantage of providing a visually attractive dental cleaning device that efficiently cleans dentures in a short time without having to brush the same and without having to soak the same for a long period of time. This rapid cleaning of the dentures is a real time saver for those on the go who do not have time to manually brush their teeth.

The present invention may, of course, be carried out in other specific ways than those herein set forth without departing from the spirit and essential characteristics of such invention. The present embodiments are, therefore, to be considered in all respects as illustrative and but not restrictive and all changes coming within the meaning equivalency range of the appended claims are intended to be embraced therein.

What is claimed is:

1. A denture cleaning device comprising: an irregular kidney shaped denture cleaning tank including an inlet end and an outlet end, said inlet end being wider than said outlet end and having a bottom with curved sidewalls about the periphery thereof; at least two liquid inlets in said inlet end of said tank disposed inwardly and upwardly from adjacent the bottom thereof directing said liquid downwardly across the surfaces of said dentures; at least one liquid outlet in the bottom of said outlet end; and means for circulating liquids placed in said tank in a continuous swirling flow from said inlets to said outlet while said irregular kidney shaped tank creates eddy currents off the main swirling flow from said inlets to said outlet whereby dentures placed in said liquid in said tank can be rapidly cleaned without soaking and without brushing.

2. The dental cleaning device of claim 1 wherein a screened filter is provided over the outlet.

3. The dental cleaning device of claim 1 wherein said device is disposed within a visually attractive housing.

4. The dental cleaning device of claim 3 wherein said visually attractive housing is constructed from furniture grade wood.

5. The dental cleaning device of claim 1 wherein the same is powered by AC electrical current which, through a converter, drives a DC current pump to circulate the liquid.

* * * * *